United States Patent [19]

Belsole

[11] Patent Number: 4,602,040

[45] Date of Patent: Jul. 22, 1986

[54] MECLOFENAMIC ACID TOPICAL PHARMACEUTICAL COMPOSITION

[75] Inventor: Susan C. Belsole, Chester, N.J.

[73] Assignee: Warner-Lambert Company, Morris Plains, N.J.

[21] Appl. No.: 719,679

[22] Filed: Apr. 4, 1985

Related U.S. Application Data

[63] Continuation-in-part of Ser. No. 485,973, Apr. 18, 1983, abandoned.

[51] Int. Cl.$^4$ ............................................. A61K 31/195
[52] U.S. Cl. ..................... 514/567; 514/825; 514/944
[58] Field of Search .................... 514/567, 825, 944

[56] References Cited

U.S. PATENT DOCUMENTS

| | | | |
|---|---|---|---|
| 3,313,848 | 4/1967 | Scherrer et al. | 260/518 |
| 4,154,833 | 5/1979 | Tauber et al. | 514/220 |
| 4,185,100 | 1/1980 | Rovee et al. | 514/171 |
| 4,206,220 | 6/1980 | Sloan | 514/419 |

FOREIGN PATENT DOCUMENTS

| | | | |
|---|---|---|---|
| 1550139 | 8/1979 | United Kingdom . | |
| 1588284 | 4/1981 | United Kingdom | 514/75 |

Primary Examiner—Stanley J. Freidman
Assistant Examiner—John W. Rollins
Attorney, Agent, or Firm—Sandra M. Person

[57] ABSTRACT

A clear gel and a cream pharmaceutical composition containing meclofenamic acid are disclosed. The clear gel composition is prepared by dissolving meclofenamic acid in polyethylene glycol monolaurate and polyethylene glycol lanolin oil and adding isopropyl alcohol with mixing and finally adding colloidal silicon dioxide with mixing. The cream composition is prepared by adding meclofenamic acid or the sodium salt thereof to an emulsion prepared by mixing a warm aqueous solution of sorbic acid with a melt of polyethylene glycol monostearate, glyceryl monostearate, caprylic and capric triglyceride and mineral oil.

The resulting compositions are indicated for the treatment of inflammation.

14 Claims, No Drawings

MECLOFENAMIC ACID TOPICAL PHARMACEUTICAL COMPOSITION

This application is a continuation-in-part of U.S. Ser. No. 485,973, filed Apr. 18, 1983, now abandoned.

The present invention relates to topically active compositions containing meclofenamic acid in a suitable topical vehicle. Also encompassed within the scope of this invention is the process for production of said topically active compositions and the treatment of inflammation by topical application of said compositions.

Although not completely understood, the effects of nonsteroidal anti-inflammatory drugs (NSAID) is thought to be due to their interference with prostaglandin biosynthesis. This activity is likely to be related to the inhibition of cyclooxygenase and lipoxygenase in arachidonic acid metabolism.

Side effects, mostly associated with gastrointestinal disturbances, have been reported with oral NSAID therapy. Topical application should be considered a valuable alternative mode of administration. Direct application to inflamed joints should result in appreciably lower systemic blood levels and hence better tolerance.

The non-steroidal anti-inflammatory drug, meclofenamic acid, its production and its use in the treatment of arthritis by oral administration is described in U.S. Pat. No. 3,313,848 issued Apr. 11, 1967, which is hereby incorporated by reference.

P. Schiantarelli et al, Arzneim-Forsch, Drug Res., 32 (1) and U.S. Pat. No. 4,185,100 describe the use of combinations containing topically active anti-inflammatory corticosteroid and non-steroidal anti-inflammatory agents for the topical treatment of cutaneous disorders.

Meclofenamic acid is virtually water-insoluble and, therefore, a hydroalcoholic gel could not be formulated at the desired concentration of drug. The drug is also insoluble in glycerin, isopropyl myristate and mineral oil. The use of the latter two solvents is described in U.S. Pat. No. 4,185,100. Its solubility in propylene glycol, ethyl alcohol and linoleic acid is somewhat less than 5%.

According to the present invention it was found that meclofenamic acid and sodium meclofenamate are soluble in the following water-miscible solvents to an extent of at best 5% at room temperature and more with the aid of heating up to 90° C.:
polyethylene glycol 400
polyethylene glycol -8 monolaurate
polyethylene glycol glucose ethers also referred to as [PEG Glucose Ethers (Glucam-E 10, P-20)]
polyethylene glycol-75 Lanolin Oil also referred to as (Lantrol AWS)
polypropylene (PPG)-5-Ceteth-10 Phosphate also referred to as (Crodafos SG)

In general polyethylene glycols and their ethers and esters—either carboxylates or phosphates—are operable when they have the requisite water-miscibility and compatibility with meclofenamic acid or its sodium salt. Mixtures are operable.

The preferred water soluble lanolin oil is a polyethylene glycol lanolin oil and the most preferred is polyethylene glycol-75 lanolin oil.

The preferred thickening agent is silicon dioxide colloidal. Other conventional thicknesses can be used in its place in combination therewith.

Useful lanolins include those containing mixed polyalkylene oxide units. Suitable lanolins are polypropylene glycol-12polyethylene glycol-50-lanolin, i.e., PPG-12-PEG-50 (Lanexal AWS), PPG-40-PEG-60 lanolin oil (Aqualose LL100) and PEG-75 lanolin (Solulan 75), and the like. Mixtures are operable.

Meclofenamic acid was found to have a highly favorable octanol/water partition coefficient and we have now discovered novel gel and cream formulations which provide maximal topical activity for meclofenamic acid.

Broadly speaking the gel formulation is a clear gel of maclofenamic acid or sodium meclofenamate in a cosolvent system of a polyethylene glycol ester, watersoluble lanolin oil, an alcohol and a thickening agent.

The polyethylene glycol ester is selected from the group of polyethylene glycol esters consisting of polyethylene glycol mono- and dilaurate and polyethylene glycol mono- and dioleate. The preferred polyethylene glycol esters are polyethylene glycol -8 monolaurate, polyethylene glycol -8 and -8 dilaurate, polyethylene glycol 400 monoleate and polyethylene glycol -8 dioleate. The most preferred polyethylene glycol ester is polyethylene glycol 400 monolaurate.

Finally, the alcohol is one or more selected from the group of 3 and 4 carbon containing alcohols consisting of propyl, isopropyl, butyl, sec-butyl and tert-butyl. Preferred alcohols are isopropyl alcohol and tert-butyl alcohol a 50/50 mixture by volume is highly preferred.

The quantity of alcohol is generally q.s. to bring the formulation to the desired weight or volume. The alcohol component will usually be present in quantities ranging from about 0 to about 75 wt %, with about 30 to about 50 weight % preferred and about 40 wt % highly preferred.

The meclofenamic acid is present in the range of about 1 to 10% by weight and preferably about 5% by weight. Sodium meclofenamate is present, in the range of about 1 to about 10, preferably 1 to 5 wt %.

The polyethylene glycol ester is present in the range of 30 to 60% by weight and preferably about 50% by weight. The water soluble lanolin is present in the range of 0 to 20% by weight and preferably about 10% by weight. The thickening agent is present from 5 to 10% by weight and preferably about 5% by weight. Sufficient alcohol is used to q.s. the formulation. Other useful solvent components include PEG-6 capric caprylic glycerides, such as Softigen 767, and the like.

The gel formulation is prepared by dissolving meclofenamic acid in a heated and stirred solution of polyethylene glycol ester and water soluble lanolin oil. The solution is allowed to cool and an alcohol is added with continued stirring until the solution cools to room temperature. A thickening agent is added with stirring and finally sufficient alcohol to make a clear gel.

The cream formulation is a homogenized emulsion of a polyethylene glycol ester, glyceryl or propylene glycol monostearate, a triglyceride, mineral oil and an aqueous solution of a preservative to which is added meclofenamic acid or the sodium salt thereof.

The polyethylene glycol ester is selected from the group consisting of polyethylene glycol monostearate and polyethylene glycol monolaurate. The preferred polyethylene glycol esters are polyethylene glycol 40, 45, 50, 75 and -6-32 monostearate and polyethylene glycol -75 and -150 monolaurate. The most preferred polyethylene glycol ester is polyethylene glycol -6-32 monostearate.

The triglyceride is selected from the group consisting of caprylic/capric triglyceride, caprylic/capric/stearic triglyceride and hydrogenated palm oil triglyceride. The preferred triglyceride is caprylic/capric triglyceride.

The preservative is selected from the group consisting of sorbic acid and benzoic acid and a combination of methylparaben and propylparaben. The preferred preservative is sorbic acid.

The meclofenamic acid or the sodium salt thereof is present in the range of about 1 to 10% by weight preferably about 5% by weight. Meclofenamic acid is the preferred form of the active ingredient.

The polyethylene glycol ester and glyceryl or propylene glycol monostearate are present in the range of 5 to 12% by weight and preferably about 9% by weight. The triglyceride is present in the range 3 to 10% by weight and preferably about 5% by weight. The mineral oil is present in the range of 5 to 10% by weight and preferably about 8% by weight.

The preservative is present in sufficient amount to function as a preservative. Usually about 0.1% by weight is sufficient.

The cream formulation is prepared by adding meclofenamic acid or the sodium salt thereof to an emulsion prepared by mixing a warm aqueous solution of preservative with a melt of a polyethylene glycol ester, glyceryl or propylene monostearate, a triglyceride and mineral oil.

The pH is adjusted to the range of about 4.5 to 5 and the cream homogenized and cooled to room temperature. If the sodium salt is used in the gel formation, the pH should be adjusted to about 4.5 to 5.0 using hydrochloric acid, or a suitable buffer, such as a citrate or acetate.

In order to further illustrate the practice of this invention, the following examples are included:

EXAMPLE 1

A clear gel containing 5% meclofenamic acid was prepared from the following ingredients:

| % | INGREDIENTS | 1000.00 g |
|---|---|---|
| 5.0 | 1. Meclofenamic Acid | 50.00 g |
| 50.0 | 2. PEG-8 Laurate (PEG 400 monolaurate) q.s. or | 500.00 g |
| 10.0 | 3. PEG-75 Lanolin Oil (Lantrol AWS) q.s. or | 100.00 g |
| 5.0 | 4. Silicon Dioxide Colloidal NF q.s. or | 50.00 g |
| — | 5. Isopropyl Alcohol USP q.s. to | 1000.00 g |

The PEG-8 laurate (polyethylene glycol 400 monolaurate) and PEG-75 lanolin oil (Lantrol AWS) was heated to 90° C. To the resulting solution was added meclofenamic acid with heating to maintain a temperature of 90° C. and with stirring until the meclofenamic acid dissolved. The solution was allowed to cool to 40° C. and 300 g. of isopropyl alcohol was added. Stirring was continued until the solution cooled to room temperature. Silicon dioxide colloidal NF was added to the solution with high mixing for 10 minutes. Sufficient isopropyl alcohol was added to make 1000 g and mixed until a uniform, clear, pale yellow gel containing 5% meclofenamic acid was obtained.

EXAMPLE 2

A gel containing 5% sodium meclofenamate is prepared according to the process of EXAMPLE 1 by replacing the meclofenamic acid with 50.00 g. of sodium meclofenamate. pH adjusted 4.5–5.0 with HCl or suitable buffer.

EXAMPLE 3

A cream containing 5% meclofenamic acid is prepared from the following ingredients:

| % | INGREDIENTS | 1000.00 g |
|---|---|---|
| 5.00 | 1. Meclofenamic Acid | 50.00 g |
| 9.00 | 2. Polyethylene Glycol-6-32 Monostearate | 90.00 g |
| 9.00 | 3. Glyceryl Monostearate | 90.00 g |
| 5.00 | 4. Caprylic/Capric Triglyceride | 50.00 g |
| 8.00 | 5. Mineral Oil | 80.00 g |
| 0.1 | 6. Sorbic Acid (preservative) | 1 g |
| — | 7. Triethanolamine q.s. to pH 4.5–5.0 | — |
| — | 8. Water, distilled q.s. to | 1,000.00 g |

The polyethylene glycol -6-32 monostearate, glyceryl monostearate, caprylic/capric triglyceride and mineral oil are combined in a suitable jacketed tank and melted by heating to 60° C.

An aqueous solution of sorbic acid is prepared in a jacketed tank equipped with a paddle mixer by dissolving the sorbic acid with mixing in the minimum amount of water preheated to 60° C. The aqueous solution of sorbic acid is added with agitation to the melted polyethylene glycol -6-32 monostearate, glyceryl monostearate, caprylic/capric triglyceride and mineral oil to form an emulsion. The meclofenamic acid is added to the emulsion with continued agitation and while maintaining the temperature at 60° C.

The pH of the resulting cream is adjusted to 4.5–5.0 with the addition of triethanolamine and the cream is circulated through an in-line homogenizer and allowed to cool to room temperature.

EXAMPLE 4

A cream containing 5% sodium meclofenamate is prepared according to the procedure of Example 3 by replacing the meclofenamic acid with 50.00 g of sodium meclofenamate. The pH is adjusted as in Example 2.

EXAMPLE 5

Method: Carrageenan edema was induced in mice by previously published methods (Levy, L., *Life Sciences* 8:601, 1969). Briefly, mice were injected in the left rear footpad with either 25 ul or 50 ul of a 1% solution of carrageenan in saline and in the contralateral footpad with a similar volume of saline. At various time intervals thereafter, the swelling was assessed in each of the rear footpads by mercury plethysmography.

In this example, female C57BL/6 or CD-1 mice were used in all studies, and swelling was assessed five hours after carrageenan injection by mercury plethysmography. Net edema was determined by subtracting the volume of the saline-injected foot from the volume of the carrageenan-injected foot. Meclofenamic acid was administered either topically or perorally one hour after carrageenan injection in a vehicle containing 50% PEG 400 monolaurate, 10 lantrol AWS, and 40% isopropyl alcohol. When applied topically, the appropriate hindpaw was dipped to the hairline in the meclofenamic acid solution or vehicle and rubbed gently for 15 seconds by a technician wearing rubber gloves. Approximately 50 ul of the meclofenamic acid or vehicle solution was used to treat each hindpaw.

Meclofenamic acid was administered orally by gavage needle in a volume of 50 ul of the monolaurate/lantrol AWS/isopropyl alcohol vehicle used above. Statistical differences in swelling between experimental groups were determined by student's t-test.

Results: When administered topically to the carrageenan-injected foot of either CD-1 or C57BL/6 mice, meclofenamic acid induced a dose-dependent reduction in swelling. The effects were maximum at the 3% concentration (49.7% inhibition) in C57BL/6 mice and at the 5% concentration (36.4% inhibition) in CD-1 mice. Because C57BL/6 mice appeared to be slightly more sensitive to the effects of meclofenamic acid, this strain was used in all subsequent studies.

EXAMPLE 6

To determine whether the observed activity of meclofenamic acid was actually due to topical rather than oral (as a result of preening) absorption, meclofenamic acid compositions (containing 1, 3 or 5% active ingredient in the above vehicle) were administered orally or topically (to the carrageenan-injected paw) and the effects on swelling were determined.

Topical meclofenamic acid was significantly ($p < 0.05$) more inhibitory than oral meclofenamic acid at the 1, 3, and 5% concentrations when applied topically to the carrageenan-injected foot than to a distant site (the saline-injected foot). These latter results suggest that the topical anti-inflammatory activity of meclofenamic acid was not due to systemic absorption.

The data from Examples 5 and 6 suggest that topically-applied meclofenamic acid has significant local anti-inflammatory activity. These effects cannot be explained in the basis of oral absorption, assuming extensive preening had occurred.

Reasonable variations, such as those which would occur to a skilled artisan, can be made herein without departing from the scope of the invention.

I claim:

1. A stable non-aqueous clear gel composition suitable for application to an inflamed joint comprising about 3 to 10% by weight meclofenamic acid, about 30 to 60% by weight of a polyethylene glycol ester, about 0 to 20% by weight of polyethylene glycol-75 lanolin oil, about 5 to 10% by weight thickening agent and sufficient alcohol to make a clear gel, wherein the polyethylene glycol ester is selected from the group consisting of polyethylene glycol mono- and dilaurate and polyethylene glycol mono- and dioleate.

2. A gel composition according to claim 1 comprising about 5% by weight meclofenamic acid.

3. A process for producing a gel according to claim 1 which comprises the steps:
   (a) dissolving meclofenamic acid in a heated and stirred solution of polyethylene glycol ester and water soluble lanolin oil
   (b) adding an alcohol and cooling to room temperature
   (c) adding a thickening agent with high shear stirring until a clear gel is obtained.

4. A method of treatment of inflammation by the topical application to inflamed joints of the meclofenamic acid gel composition of claim 1.

5. A cream composition suitable for application to an inflamed joint comprising about 1 to 10% by weight meclofenamic acid, about 5 to 12% by weight polyethylene glycol ester, about 5 to 12% by weight glyceryl or propylene monostearate, about 3 to 10% by weight of a triglyceride, about 5 to 10% by weight mineral oil and about 0.1% by weight preservative, wherein the polyethylene glycol ester is selected from the group consisting of polyethylene glycol monostearate and polyethylene glycol monolaurate; the triglyceride is selected from the group consisting of caprylic/capric triglyceride, caprylic/capric/stearic triglyceride and hydrogenated palm oil triglyceride; and the preservative is selected from the group consisting of sorbic acid and benzoic acid and a combination of methylparaben and propylparaben.

6. A cream composition according to claim 5 comprising about 5% by weight meclofenamic acid.

7. A process for producing a cream according to claim 5 which comprises the steps:
   (a) melting a mixture of polyethylene glycol ester, glyceryl or propylene monostearate, a triglyceride and mineral oil
   (b) adding an aqueous solution of a preservative with mixing to form an emulsion
   (c) adding meclofenamic acid to the emulsion with agitation and
   (d) adjusting the pH to 4.5 to 5.0.

8. A method of treatment of inflammation by the topical application to an inflamed joint of the meclofenamic acid cream composition of claim 5.

9. A stable non-aqueous clear gel composition suitable for application to an inflamed joint comprising about 3 to 10% by weight of sodium meclofenamate, about 30 to 60% by weight of polyethylene glycol ester, about 0 to 20% by weight polyethylene glycol-75 lanolin oil, about 5 to 10% by weight thickening agent and sufficient alcohol to make a clear gel, wherein the polyethylene glycol ester is selected from the group consisting of polyethylene glycol mono- and dilaurate and polyethylene glycol mono- and dioleate.

10. A method of treatment of inflammation by the topical application to an inflamed joint of the sodium meclofenamate gel composition of claim 9.

11. A process for producing a gel according to claim 9 which comprises the steps:
   (a) dissolving sodium meclofenamate in a heated and stirred solution of polyethylene glycol ester and lanolin oil,
   (b) adding an alcohol and cooling to room temperature, and
   (c) adding a thickening agent with high shear stirring until a clear gel is obtained.

12. A cream composition suitable for application to an inflamed joint comprising about 3 to 10% by weight of sodium meclofenamate, about 30 to 60% by weight glyceryl or propylene glycol ester, about 5 to 12% by weight of a triglyceride, about 5 to 10% by weight mineral oil and about 0.1% by weight preservative, wherein the polyethylene glycol ester is selected from the group consisting of polyethylene glycol 40, 45, 50 and 75 and -6-32 monostearate and polyethylene glycol-75 and -150 monolaurate and the triglyceride is selected from the group consisting of caprylic/capric triglyceride, caprylic/capric/stearic triglyceride and hydrogenated palm oil triglyceride.

13. A process for producing a cream according to claim 12 which comprises the steps:
   (a) melting a mixture of polyethylene glycol ester, glyceryl or propylene monostearate, a triglyceride and mineral oil;
   (b) adding an aqueous solution of a preservative with mixing to form an emulsion;
   (c) adding sodium meclofenamate to the emulsion with agitation; and
   (d) adjusting the pH to 4.5 to 5.0.

14. A method of treatment of inflammation by the topical application to an inflamed joint of the sodium meclofenamate cream composition of claim 12.

* * * * *